United States Patent
Scaiano et al.

(10) Patent No.: US 10,685,138 B2
(45) Date of Patent: Jun. 16, 2020

(54) RE-IDENTIFICATION RISK MEASUREMENT ESTIMATION OF A DATASET

(71) Applicant: PRIVACY ANALYTICS INC., Ottawa (CA)

(72) Inventors: Martin Scaiano, Ottawa (CA); Stephen Korte, Ottawa (CA); Andrew Baker, Alcove (CA); Geoffrey Green, Ottawa (CA); Khaled El Emam, Ottawa (CA); Luk Arbuckle, Ottawa (CA)

(73) Assignee: PRIVACY ANALYTICS INC., Ottawa, ON (CA)

( * ) Notice: Subject to any disclaimer, the term of this patent is extended or adjusted under 35 U.S.C. 154(b) by 0 days.

(21) Appl. No.: 15/320,240

(22) PCT Filed: Apr. 1, 2016

(86) PCT No.: PCT/CA2016/050381
§ 371 (c)(1),
(2) Date: Dec. 19, 2016

(87) PCT Pub. No.: WO2017/008144
PCT Pub. Date: Jan. 19, 2017

(65) Prior Publication Data
US 2018/0114037 A1    Apr. 26, 2018

Related U.S. Application Data

(60) Provisional application No. 62/193,024, filed on Jul. 15, 2015.

(51) Int. Cl.
*G06F 21/00* (2013.01)
*G06F 21/62* (2013.01)
(Continued)

(52) U.S. Cl.
CPC ........ *G06F 21/6254* (2013.01); *G06F 16/219* (2019.01); *G06F 21/604* (2013.01); *G16H 10/60* (2018.01)

(58) Field of Classification Search
CPC ...... G06F 21/6254; G06F 21/60; G16H 10/60
See application file for complete search history.

(56) References Cited

U.S. PATENT DOCUMENTS 9,442,980 B1    9/2016 Trepetin
2002/0169793 A1*  11/2002 Sweeney ........... G06F 17/30424
(Continued)

OTHER PUBLICATIONS

Emam, K. E., Dankar, F. K., Vaillancourt, R., Roffey, T., & Lysyk, M. (2009). Evaluating the Risk of Re-identification of Patients from Hospital Prescription Records. The Canadian Journal of Hospital Pharmacy, 62(4), 307-319. (Year: 2009).*
(Continued)

*Primary Examiner* — Alexander Lagor
(74) *Attorney, Agent, or Firm* — John Maldjian; Maldjian Law Group LLC

(57) ABSTRACT

There is provided a system and method executed by a processor for estimating re-identification risk of a single individual in a dataset. The individual, subject or patient is described by a data subject profile such as a record in the dataset. A population distribution is retrieved from a storage device, the population distribution is determined by one or more quasi-identifying fields identified in the data subject profile. An information score is then assigned to each quasi-identifying (QI) value of the one or more quasi-identifying fields associated with the data subject profile. The assigned information scores of the quasi-identifying values for the data subject profile are aggregated into an aggregated information value. An anonymity value is then calculated from the aggregated information value and a size
(Continued)

of a population associated with the dataset. A re-identification metric for the individual from the anonymity value is then calculated.

17 Claims, 10 Drawing Sheets

(51) Int. Cl.
*G06F 16/21* (2019.01)
*G06F 21/60* (2013.01)
*G16H 10/60* (2018.01)

(56) References Cited

U.S. PATENT DOCUMENTS

| | | | |
|---|---|---|---|
| 2003/0061510 A1 | 3/2003 | Hartmann | |
| 2010/0077006 A1 | 3/2010 | El Emam et al. | |
| 2010/0100577 A1 | 4/2010 | Middleton | |
| 2010/0114840 A1* | 5/2010 | Srivastava | G06F 17/30536 707/688 |
| 2010/0332537 A1 | 12/2010 | El Emam et al. | |
| 2011/0178943 A1* | 7/2011 | Motahari | G06F 21/6254 705/325 |
| 2011/0258206 A1* | 10/2011 | El Emam | G06F 21/577 707/754 |
| 2014/0019194 A1 | 1/2014 | Anne | |
| 2014/0081652 A1 | 3/2014 | Klindworth | |
| 2014/0189858 A1* | 7/2014 | Chen | G06F 17/30289 726/22 |
| 2014/0304244 A1* | 10/2014 | Toyoda | G06F 21/6254 707/696 |
| 2015/0007249 A1 | 1/2015 | Bezzi | |
| 2015/0033356 A1 | 1/2015 | Takenouchi | |
| 2015/0067602 A1 | 3/2015 | Bernstein | |
| 2015/0128285 A1* | 5/2015 | LaFever | H04L 67/02 726/26 |
| 2015/0169895 A1 | 6/2015 | Gkoulalas-Divanis et al. | |
| 2015/0356591 A1 | 12/2015 | Fano | |
| 2016/0034703 A1* | 2/2016 | Dubov | G06F 17/3053 726/27 |
| 2016/0203172 A1* | 7/2016 | Attaluri | G06F 17/30324 707/745 |
| 2016/0248799 A1 | 8/2016 | Ng | |
| 2017/0243028 A1 | 8/2017 | LaFever | |
| 2018/0114037 A1* | 4/2018 | Scaiano | G06F 21/604 |

OTHER PUBLICATIONS

El Emam, K., Brown, A., AbdelMalik, P., Neisa, A., Walker, M., Bottomley, J., & Roffey, T. (2010). A method for managing re-identification risk from small geographic areas in Canada. BMC medical informatics and decision making, 10, 18. doi:10.1186/1472-6947-10-18.*

Bezzi, M., "An Entropy based method for measuring anonymity", Proceedings of the IEEE Third International Conference on Security and Privacy in Communications Networks and the Workshops, SecureComm 2007, Nice, France, (5 pages total) (Sep. 17, 2007).

Diaz, C. et al., "Information Theory and Anonymity", Proceedings of the 23rd Symposium on Information Theory in the Benelux, Louvain la Neuve, Belgium, (8 pages total) (May 29, 2002).

Kounine, A. et al., "Assessing Disclosure Risk in Anonymized Datasets", Proceedings of FloCon2008, Savannah, Georgia, USA, (4 pages total) (Jan. 7, 2008).

Serjantov, A. et al., "Towards an Information Theoretic Metric for Anonymity", Proceedings of the Second International Workshop on Privacy Enhancing Technologies, PET 2002, San Francisco, CA, USA, (14 pages total) (Apr. 14, 2002).

Diaz, C. et al., "Towards measuring anonymity", Proceedings of the Second International Workshop on Privacy Enhancing Technologies, PET 2002, San Francisco, CA, USA, (15 pges total) (Apr. 14, 2002).

Trabelsi, S. et al., "Data Disclosure Risk Evaluation", Proceedings of the Fourth International Conference on Risks and Security of Internet and Systems (CRiSIS 2009), Toulouse, France, pp. 35-42, (8 pages total) (Oct. 19, 2009).

Toth, G. et al., "Measuring Anonymity Revisited", Proceedings of the Ninth Nordic Workshop on Secure IT, Espoo, Finland, (6 pages total), (Nov. 4, 2004).

Airoldi, E.M. et al., "An entropy approach to disclosure risk assessment: Lessons from real applications and simulated domains", Decision Support Systems, vol. 51, issue 1, pp. 10-20, Apr. 1, 2011 (11 pages total).

International Search Report and Written Opinion dated Jun. 5, 2016 issued in connection with International Application No. PCT/CA2016/050381 (10 pages total).

* cited by examiner

US 10,685,138 B2

RE-IDENTIFICATION RISK MEASUREMENT ESTIMATION OF A DATASET

CROSS-REFERENCE TO RELATED APPLICATION

This application is a 371 application which claims benefit and priority to International Application No. PCT/CA2016/050381, filed Apr. 1, 2016, which claims priority to U.S. Provisional Application No. 62/193,024 filed Jul. 15, 2015, the entirety of which is hereby incorporated by reference for all purposes.

TECHNICAL FIELD

The present disclosure relates to datasets containing personally identifiable information and in particular to risk assessment of the datasets.

BACKGROUND

Personal information is being continuously captured in a multitude of electronic databases. Details about health, financial status and buying habits are stored in databases managed by public and private sector organizations. These electronic databases contain information about millions of people, which can provide valuable research, epidemiologic and business insight. For example, examining a drugstore chain's prescriptions can indicate where a flu outbreak is occurring. To extract or maximize the value contained in these databases, data custodians must often provide outside organizations access to their data. In order to protect the privacy of the people whose data is being analyzed, a data custodian will "de-identify" or "anonymize" information before releasing it to a third-party. An important type of de-identification ensures that data cannot be traced to the person about whom it pertains, this protects against 'identity disclosure'.

When de-identifying records, many people assume that removing names and addresses (direct identifiers) is sufficient to protect the privacy of the persons whose data is being released. The problem of de-identification involves those personal details that are not obviously identifying. These personal details, known as quasi-identifiers (QIs), include the person's age, sex, postal code, profession, ethnic origin and income, financial transactions, medical procedures (to name a few). To be able to de-identify data the assessment of the risk of re-identification is required to be determined. Further, the size of the datasets can contain a vast number of entries requiring a computer processor to be able analyze the data.

Accordingly, systems and methods that enable improved risk assessment remains highly desirable.

SUMMARY

In accordance with an aspect of the present disclosure there is provided a system and method executed by a processor for estimating re-identification risk of a single individual in a dataset, the individual described by a data subject profile in the dataset, the method comprising: retrieving a population distribution from a storage device, the population distribution determined by one or more quasi-identifying fields identified in the data subject profile; assigning an information score to each quasi-identifying value of the one or more quasi-identifying fields associated with the data subject profile; aggregating the assigned information scores of the quasi-identifying values for the data subject profile into an aggregated information value; calculating an anonymity value from the aggregated information value and a size of a population associated with the dataset; and calculating re-identification metric for the individual from the anonymity value.

In a further embodiment of the system and method, the information score is defined by a number of information binary bits provided by the quasi-identifying value.

In a further embodiment of the system and method, an aspect calculating an anonymity value from an information score is defined as a=reid_bits−given_bits where reid_bits is a number of re-identification bits calculated from the size of the population using reid_bits=$\log_2$ (population) and given_bits describes the aggregated information value available for re-identification of the data subject profile.

In a further embodiment of the system and method, the population distribution is a single variable or multi-variable distribution, which maps value to a probability of an individual having that value.

In a further embodiment of the system and method, further comprising creating an aggregate result of a plurality of re-identification metric for a plurality of data subject profiles on a larger dataset.

In a further embodiment of the system and method, creating the aggregate result for the data subjects in a single value result.

In a further embodiment of the system and method, the aggregate result is an arithmetic average.

In a further embodiment of the system and method, wherein the aggregate result is a multi-valued summary.

In a further embodiment of the system and method, wherein the multi-valued summary is an array or matrix of results.

In a further embodiment of the system and method, wherein creating the aggregate information scores is a summation of information scores for the subject.

In a further embodiment of the system and method, wherein the information scores in each data subject profile is summed to obtain a total information value contained in all child records for a given parent data subject profile.

In a further embodiment of the system and method, wherein the data subject profile comprises a record, the method further comprising: aggregating information scores within the record; aggregating information score from related records from within a child table associated with the record; and aggregating information score from the child table.

In a further embodiment of the system and method, further comprising selecting a pre-defined number of data elements with the most information related to a given parent as defined by the information score.

In a further embodiment of the system and method, further comprising calculating an arithmetic average information (u) in all elements related to a given parent data subject profile.

In a further embodiment of the system and method, wherein calculating re-identification metric is defined a value associated with anonymity, equivalence class size, or re-identification risk.

In a further embodiment of the system and method, further comprising the evaluation of the ability to unambiguously link a record in one dataset to identify a matching individual in another dataset.

In a further embodiment of the system and method, wherein anonymity value is a metric measured in bits, where if the anonymity value is greater than zero there are many individuals who would match this record in the population, if the anonymity is equal to zero the individual is unique in the population, and if the anonymity value is less than zero the individual is unlikely to exist in the dataset or population.

In a further embodiment of the system and method, further comprising generating a histogram from a plurality of calculated anonymity values to estimate a number of data subjects who are unique in the dataset.

BRIEF DESCRIPTION OF THE DRAWINGS

Further features and advantages of the present disclosure will become apparent from the following detailed description, taken in combination with the appended drawings, in which.

DETAILED DESCRIPTION

Embodiments are described below, by way of example only, with reference to FIGS. 1-10.

An information theory based replacement is provided for traditional risk measures, such as k-anonymity, or expected number of correct re-identifications, or re-identification risk. K-anonymity based methods compare records or data subjects within dataset to one another. If the dataset is a sample of an electronic database, then risk associated with the dataset is then extrapolated to a larger population contained in the electronic database. The disclosed computer system and computer implemented method directly estimates the risk of a record against a population and does not compare individuals against one-another but against a population, which allows this method to process a single record without a dataset being processed in order to provide a risk assessment. The system and method are effective at generating a risk measure because it can account unequal probabilities of matching records. For example, consider a probabilistic matching scheme which finds the most likely match, the mutual information can be used to measure and validate that a dataset is l-diverse. Entropy has been proposed for use in disclosure control of aggregate data, which predicts an attacker's ability to impute a missing value or values from views on the same data. Entropy can be used to estimate the average amount of information in QI and how the size of the population limits the amount of information that can be released about each subject.

The system and method disclosed take as input one or more subject profiles to determine risk of the dataset. The individual person is a subject or patient present in a dataset. The data of a subject profile is a description of the individual in structured form. The structure may be expressed in a database, extensible mark-up language (XML), JavaScript Object Notation (JSON), or another structured format. The subject profile consists of fields and associated values that describe the subject. For example a subject profile may contain date of birth, province or state of residence, gender. Furthermore, a subject profile may contain "longitudinal data" (or temporal data) which either changes in time or describes an event at a particular time. Examples of longitudinal data, might be information about a hospital visit (admission data, length of stay, diagnosis), financial transactions (vendor, price, date, time, store location), or an address history (address, start date, end date).

Figure 1:
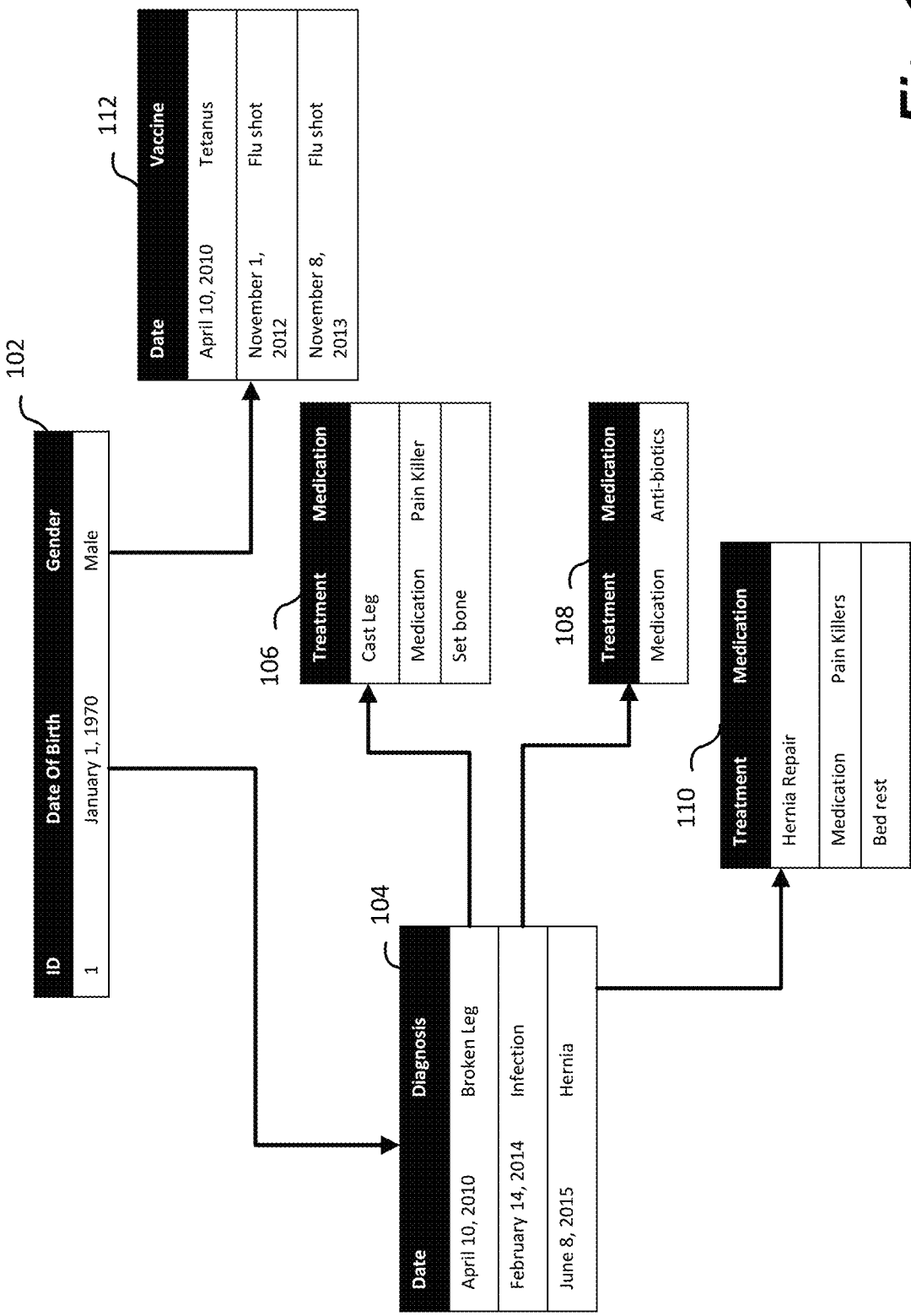
FIG. 1 shows an example data subject profile that may be processed by the disclosed method and system.

An example data subject profile is shown in FIG. 1. Element 102 contains the top level subject information such as demographic information. Element 104 contains longitudinal data describing various doctors' visits. There are many doctors' visits related to a single subject. For each doctors' visit, there are child elements 106, 108, 110, which describe the treatment from each visit. Notice again there may be many treatments for a single visit. In a database, elements 106, 108, and 110 would normally be in a single table. Connected to the subject demographics there are also a number of vaccination events listed 112.

A data subject profile may in fact be data extracted from a text file and assigned to certain meaningful fields. If a dataset is being processed that contains multiple individuals they are not required to have the same field. By not requiring the same fields to be present enables processing of unstructured, semi-structured and textual dataset, where individuals may not have the same schema.

Often when data is stored in a database, XML, or JSON format there is a schema which defines, which fields exists, what they contain, and any relationships between fields, elements, records, or tables. The relationships are usually of the form 1-to-1 or 1-to-many. For example consider the relationship between a subject and DOB, Gender(1-to-1), or subject and some financial transactions (1-to-many). There are scenarios where many-to-many and many-to-one relations exist and these should not be excluded, however the disclosed examples provided will focus on the more common relationships within a subject profile.

In disclosure control and risk measurement each field in a schema is classified into direct-identifiers (DI), quasi-identifiers (aka indirect identifiers) (QI), and non-identifiers (NI). The system can generically apply to any value regardless of classification, however QIs (or QI fields) will be referred to as this is normally utilized in risk measurement.

Figure 2:
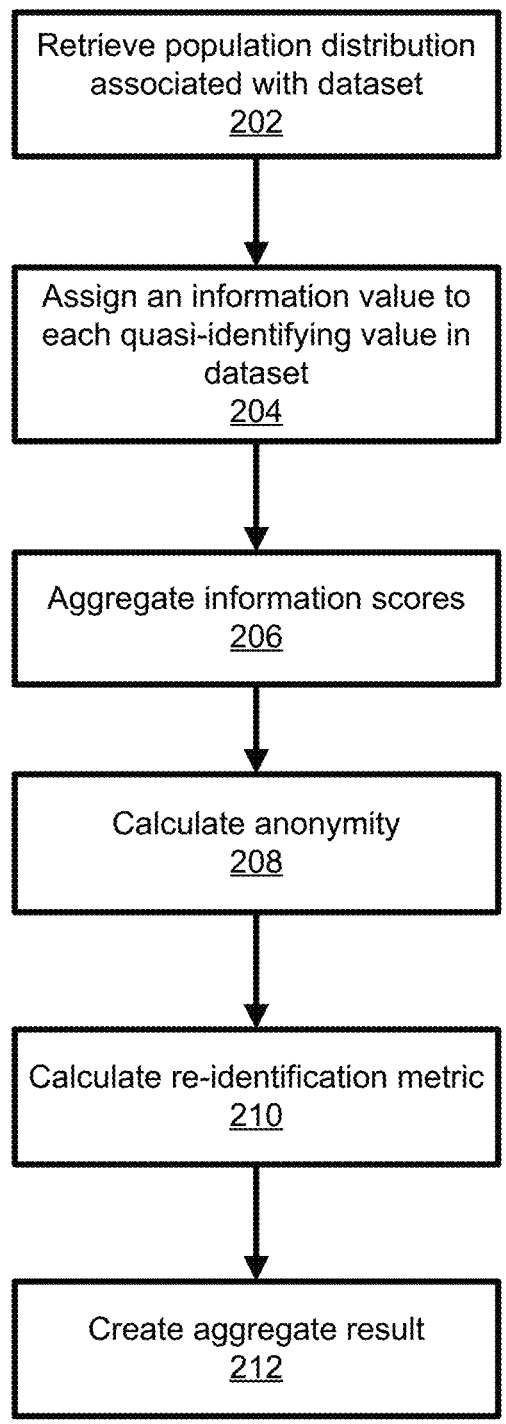
FIG. 2 shows a flowchart for a method of estimating re-identification risk of a single individual in a dataset.

Referring to FIG. 2, a population distribution for each QI in the schema is retrieved (202) from a storage device. A population distribution may be associated with one or more QIs and multiple distributions may be required for the schema. The population distribution is associated by the type of data contained in the dataset. For example the population distribution may be from census data which can be determined based upon the QI in the schema. The association of the dataset with population distributions may be determined automatically by analyzing content of the dataset or by predefined associations. A population distribution maps a value to probability, which represents the probability of someone in the population having this value.

Once a distribution for each QI is acquired, each value in a data subject profile is assigned an information score (204). Information scores are measured in bits and based on information theory. For example the sex of the subject may be expressed as 1-bit of data, male or female, whereas an alphanumeric postal code having 3 numbers and 3 letters would be 24 bits, where A-Z is 4.7 bits=$\log_2(26)$, 0-9 is 3.3 bits=$\log_2(10)$ and the postal code could be 4.7+3.3+4.7+3.3+4.7+3.3=24 bits. However not all of those postal codes are in use, so if the number of postal codes in use is 845,990 the number of bits where information in postal code is $\log_2(845,990)$=19.7 bits. Further the specific population per postal code could reduce the number of bits, for example a specific postal code K1G4J4 has a population of 4,076, where Canada has a population of 35 million, so the information in K1G4J4 is $\log_2(4076/35\ million)$=13 bits. Although a postal code calculation of information bits is described the method of determining the number of information bits is applicable to other QIs in a similar manner.

Aggregation of information scores is performed to create a single information score from several values (206). There are several different aggregation techniques, each serves to model certain types of relationships. Aggregation techniques can be composed where one aggregation technique uses the results of other aggregation techniques. Regardless the complexity of a schema, the end result is a single information score that is measured in bits, which describes the accumulated or total information available for re-identification of the data subject. The resulting single value is referred to as the given_bits.

Anonymity can then be calculated using given_bits and the population size as input (208). The equation for anonymity (a) is a=reid_bits−given bits where reid_bits is the number of re-identification bits, is calculated from size of the population using the following equation reid_bits=$\log_2$(population). The population is the group of subjects from which the subject profile (or dataset) is sampled. For example, if a dataset contains a random sample of voters then the population is the total number of voters.

Most measures use equivalence class size (k), which cannot be less than 1; at minimum an individual person is considered unique. Anonymity can measure beyond uniqueness (negative anonymity or zero anonymity is unique). Negative anonymity suggests a person is unique usually even on a subset of their subject profile. The magnitude of negative anonymity indicates how much suppression or generalization by de-identification techniques will be required to have the person look like another person in the population. Anonymity can be used to establish the probability that someone else would look like this person. Negative anonymity can be used to determine if there is sufficient information to link records across dataset with a significant confidence level.

There are several re-identification metrics that can be used to calculate from anonymity. Anonymity can be converted to equivalence or similarity class size and re-identification risk. All of these metrics are established standards, with the exception of anonymity introduced here. A result of the process defined here is that the risk is measured on an individual, not on a dataset. Other methodologies focus on measuring re-identification metrics on datasets, but cannot necessarily assign a risk to a data subject in a dataset or an individual data subject (i.e. dataset of 1 data subject). This enables processing subject profiles individually, leading to linear time processing, instead of other k-anonymity methods, which are usually quadratic or worse processing times. Furthermore, this enables measuring re-identification metric of profiles coming from text documents, which are not contained in a dataset or having a common schema.

For all the following examples, let a be the anonymity of the given subject where Equivalence (or similarity) class size (k) is calculated as k=$2^{max(a,0)}$. The re-identification risk using the following formula reid_risk=$2^{-max(a,0)}$ is calculated (210). The re-identification risk may be presented for the associated record. Alternatively the resulting calculated re-identification metric (210) can be aggregated (212) into a whole for the dataset to create an aggregate result. The aggregation method utilized depends on the re-identification metric and the data model being considered and will be discussed below.

Re-identification Risk can be an average risk of someone randomly choosing a record from the dataset and trying to re-identify it in the population, that is a simple arithmetic average. This average risk is calculated as $$\text{average\_reid\_risk} = \frac{1}{n}\sum_{i=1}^{n}\text{reid\_risk}_i$$

where is n the total number of data subjects in the sample, i iterates over each data subject, and reid_risk, is the risk of re-identification for subject (i).

Re-identification Risk can be an average risk of someone randomly choosing a subject in the population and trying to re-identify their record in the dataset. This average is the number of equivalence classes divided by the population size. The equation is $$\text{average\_reid\_risk} = \frac{\sum_{i=1}^{n}\frac{1}{k_i}}{\sum_{i=1}^{n}\frac{K_i}{k_i}}$$

where is n the total number of data subjects in the sample, i iterates over each data subject, $K_i$ and $k_i$ are the number of records matching a subject in the sample, wherein calculating the risk of re-identification may be replaced with calculating the number of data subjects matching this record (k) using the following equation k=$2^{max(a,0)}$ (k value) and using sample instead of population measurement, respectively.

Further the anonymity may be aggregated into histogram. Since anonymity is normally a real value (i.e. continuous or decimal) if anonymity values are converted into an integer value, the anonymity profile of dataset can be concisely expressed. In part, this is because anonymity is in a logarithmic scale, expressing magnitudes of difference. However, operations like round, round-up (ceil), round-down (floor), will change the average risk profile of the histogram. A first histogram models population anonymity and maintains the average risk profile of the sample to population re-identification. Let H[. . . ] be the histogram. H[a]=x where a is an integer anonymity value and x is non-negative real value indicating the number of people with this anonymity. For each subject let the anonymity of the subject contributed to the histogram be:

$z$=floor($a$)

$d$=$a$−$z$ $p$=$2^{1-d}$−1

$H[z]$=$H[z]$+p $H[z+1]$=$H[z+1]$+(1−$p$)

This histogram is an effective tool for estimating the number of data subjects with a particular anonymity. A common use for this would be to estimate the number of data subjects who are unique. The number of unique data subjects is $$= \sum_{i=1}^{i<=0} H[i]$$

where 1 is the lowest anonymity value in the histogram.

The second histogram models sample and population anonymity and maintain the average risk profile of the population to sample re-identification. A two-dimensional histogram describes the population and sample anonymity as a matrix of values, the row and column number represent integer anonymity values for the population and sample, while the cells contain real values indicating the number of people with this (population, sample) anonymity.

Let $A_i$ be the population anonymity of data subject i
Let $a_i$ be the sample anonymity of data subject i
Let H[x][y]=z be a cell in the histogram.
x is the population anonymity as an integer value
y is the sample anonymity as an integer value
z is a non-negative real value indicating the number of people with anonymity x,
y $\forall\, i \in$ individuals $z_{pop} = \text{floor}(A_i)$ $z_{samp} = \text{floor}(a_i)$ $d_{pop} = A_i - z_{pop}$ $d_{samp} = a_i - z_{samp}$ $p_{samp} = 2^{1-d_{pop}} - 1$ $p_{pop} = \dfrac{-2 * (2^{d_{pop}-d_{samp}} - p_{samp} - 1)}{1 + p_{samp}}$ $H[z_{pop}][z_{samp}] \mathrel{+}= p_{pop} * p_{samp}$ $H[z_{pop}][z_{samp} + 1] \mathrel{+}= p_{pop} * (1 - p_{samp})$ $H[z_{pop} + 1][z_{samp}] \mathrel{+}= (1 - p_{pop}) * p_{samp}$ $H[z_{pop} + 1][z_{samp} + 1] \mathrel{+}= (1 - p_{pop}) * (1 - p_{samp})$ A population distribution defines a mapping of quasi-identifying values to the probabilities of those values occurring in the range, region, or demographic profile covering the data subjects associated with/contained within the dataset. The algorithm is agnostic of the source of the priors, however a number of methods are defined to obtain priors including Estimated Sample Distribution (ESD) measurement.

A population distribution may be derived from census data or other pre-existing data sources. The probability of value (pr(v)) is defined as $$pr(v) = \dfrac{populationHaving(v)}{population}$$

A population distribution may be approximated using the distribution from the dataset. The method for estimating population distributions using sample data is provided by determining the sample distribution, this is a map of values to the number of people with this value. Each value is classified as common or rare. Common values occur when more than X individuals have that value in the sample distribution. Rare values occur when a value is associated with X or less data subjects in the sample distribution where X is normally set to 1. Thus to the total number of values is the sum of the rare values and common values. Total Values=RareValues$_{sample}$+CommonValues The total number of values (Estimated Values) is estimated including unseen values, that is values that did not occur in the data (sample) but occur in the population. Estimation of the total number of values can use, but is not limited to species estimators, such as Bias Chao estimator or Abundance Coverage-based Estimator (ACE). These estimators are dependent on the distribution selected.

Alternatively, a distribution may be compared against a standard distribution, such as a uniform distribution or normal distribution. If they match in shape within a certain tolerance (error), then information about the sample distribution can be used to estimate the number of values that have not been seen. Assuming all unseen values are in fact rare values the number of rare values in the population is calculated where RareValues$_{pop}$=EstimatesValues−CommonValues.

The resulting population distribution for a common value is the probability of value occurring in the sample distribution. Consider common values are well-represented and the sample distribution should be a good estimate of the population, so $pr_{pop}(v_{common})$=$pr_{sample}(v)$, where $pr_{sample}(v)$ is the sample probability and $pr_{pop}(v)$ is the population probability.

For the resulting population distribution for rare values, find the frequency of the value of the sample distribution and correct this for the probability that this value was randomly selected to be included in the dataset. The intuition is that the rare values that are in the data made it by chance and need to be accounted for the chance of rare value having made it in to the dataset.

$$pr_{pop}(v_{rare}) = pr_{sample}(v_{rare}) * \dfrac{rareValues_{sample}}{rareValues_{pop}}$$

A population distribution may be approximated using a uniform distribution. Given the size of the value space (how many values are possible), then assume the probability of any given value is 1/NumberOfValues. On average this leads to an overestimate of the risk of re-identification (a conservative assumption), however on any individual case it can underestimate or overestimate the probability of a value and lead to under or overestimation of risk.

A distribution may be based on known or published averages. This average may be returned as the probability for a value occurring, which satisfy the value specificity. For example a publication may claim that "80% of Canadians see a doctor at least once a year". The probability would be 80% and the specificity is 1 year. The population distribution can return that the year (date without month or day) of a doctor's visit has an 80% probability (i.e. 80% of the population visited a doctor that year).

A distribution based on known or published averages may be made more granular (more specific) by combining a known average and uniform distribution over the specificity.

As with the previous example, 80% is the probability and 1 year is the specificity, however the values are in days. The probability can be estimated of a particular subject visiting a doctor on a particular day as (assuming 365 days in a year) 80%÷365=0.8÷365=0.2%.

A joint distribution may be used to more accurately model probabilities and correlations between values. The probability of set/combination of quasi-identifier values occurring can be expressed as the joint distribution over two or more quasi-identifying values. A joint quasi-identifier may be defined as a tuple of values, for example a zip code and date of birth (90210, April 1 1965). A joint distribution of the quasi-identifiers can be used to calculate the probability of this combination of values occurring. A joint distribution may be acquired by any methods for acquiring a population distribution.

A method for assigning an information score (measured in bits) is to calculate $I(v)=-\log_2(pr(v))$ where v is the value, $I(v)$ is the information score for the value, and $pr(v)$ is the probability of the value occurring in the population distribution.

A method for assigning an information score (measured in bits) can incorporate the expected (probable or likely) knowledge of an average adversary. The method assumes a probability of knowing a particular value is given. Let $0 \leq k(v) \leq 1$ be the probability that someone would know value v. For example, if v is a birth event, it is likely to be known or in the public domain ($k(v)=1$), while a sinus infection is not particularly knowable or memorable ($k(v)<1$). The expected information from value $I(v)$ can be calculated as $I(v)=-\log_2(pr(v))*k(v)$ Assigning an information score (measured in bits) can incorporate the probability of knowing a value and compute the weighted average risk of all combinations of knowledge scenarios. For a set of values ($V=\{v_1, v_2, \ldots, v_{n-1}, v_n\}$), a knowledge scenario (KS) is the set of values known by an adversary ($KS \subseteq V$). The set of all knowledge scenarios is the power set of V (i.e. $P(V)$). Let the probability of a particular value being known be $k(v_i)$. Let the risk associated with a knowledge scenario be $risk(KS)$. The weight average of all knowledge scenarios is $$\text{average} = \sum_{\forall s \in P(V)} \left( R(s) \left( \prod_{v \in s} k(v) \right) \left( \prod_{v \in V \wedge v \notin s} (1-k(v)) \right) \right).$$

Because the power set is combinatorial, then the previous equation is combinatorial in computation, however, the equation can be factored into terms leading linear processing if the following equation is used for the information in each value $I(v)=\log_2(k(v)*pr(v)+(1-k(v)))$.

Consider the following example where $V=\{v_1, v_2\}$ then average=$k(v1)k(v2)R(v1, v2)+k(v1)(1-k(v2))R(v1)+$
$(1-k(v1))k(v2)R(v2)+(1-k(v1))(1-k(v2))R(\ )$ If $R(v1, v2)=2^{I(v1)I(v2)-reid\_bits}$ then the equation becomes average=$k(v1)k(v2)2^{I(v1)I(v2)-reid\_bits}+k(v1)(1-k(v2))2^{I(v1)-reid\_bits}+(1-k(v1))k(v2)2^{I(v2)-reid\_bits}+(1-k(v1))(1-k(v2))2^{-reid\_bits}$ average=$2^{-reid\_bits}(k(v1)2^{I(v1)}+1-k(v1))(k(v2)2^{I(v2)}+1-k(v2))$ This result is computationally significant, simplifying combinatorial processing to linear.

Values can be aggregated into a single information score for a data subject. This score is referred to as the given_bits for the data subject. A number of methods are described below, however this list is neither complete nor limiting. New aggregations scheme can be introduced to the methodology.

Aggregation of Total Knowledge is a method where information scores for values are summed together resulting in the total information. Assume there are n values indexed from 1 . . . n. Then the total information score (given_bits) is $$\text{given\_bits} = \sum_{i=1}^{n} I(v_i)$$

Simple Mutual Information is a method where information scores are aggregated yet account for correlations. In information theory correlation is expressed as mutual information. The relationship between two values is expressed in pointwise mutual information. If the values are correlated, that is they tend to co-occur, then the total information from the two value is less than the sum of the two independent values. This occurs because one value may be inferred from another value, thus knowing the second value does not increase information.

Assuming there are n values indexed from 1 . . . n this method requires joint distributions as previously described. Assuming that joint distributions are provided for all pairwise combinations of values from 1 . . . m where m<n a set PV of all pairs of values ($v_i, v_j$) where $i \in \{1 \ldots m\}$, $j \in \{1 \ldots m\}$, $i \neq j$ is constructed. For each pair ($v_i, v_j$)$\in$PV the pointwise mutual information (PMI)

$$PMI(v_i, v_j) = -\log_2\left(\frac{pr(v_i, v_j)}{pr(v_i)pr(v_j)}\right)$$

where $pr(v_i, v_j)$ is the value from the joint distribution that is calculated. A subset of pairs (SPV) from PV where SPV$\subseteq$PV is calculated. The given_bits for values 1 . . . n is calculated. This may be done via the method of Aggregation of Total Knowledge, but is not limited to this. For each pair ($v_i, v_j$)$\in$SPV the pointwise mutual information is added to given_bits where $$\text{given\_bits}' = \text{given\_bits} + \sum_{(v_i, v_j) \in SPV} PMI(v_i, v_j).$$

given_bits' is then aggregated to an information score accounting for mutual information.

Figure 3:
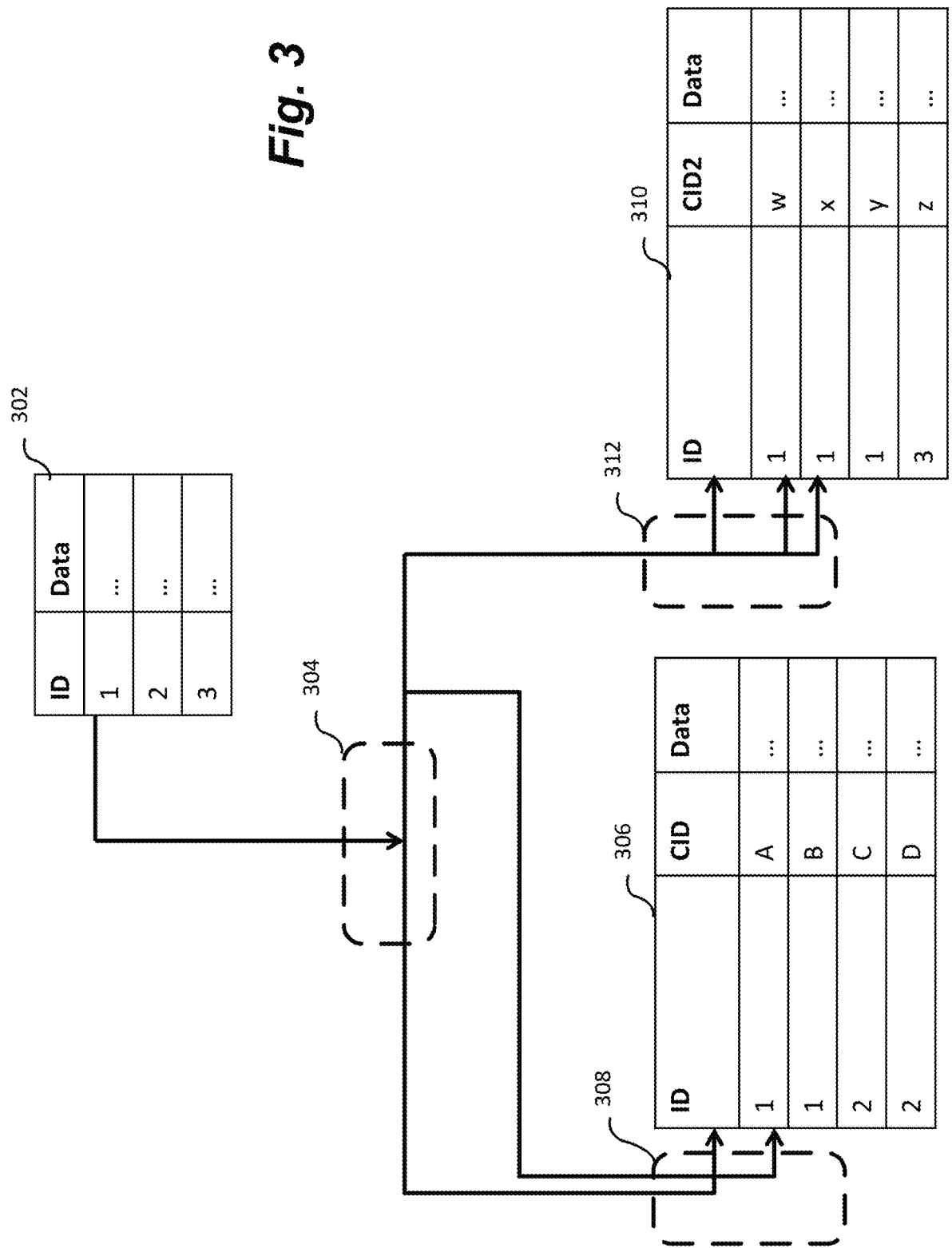
FIG. 3 shows a representation of complex schema aggregation method.

A general and extensible method for aggregating information score in complex schema consisting of multiple table (or table like elements) is described. A dataset may be expressed as a schema, which has tables and relations between tables. For practical purposes the model is described as if it was in a database forming a directed acyclic graph. For the purposes of this method and risk measurement, the top or root table 302 would be the subject table, since all measurements are based on subjects as shown in FIG. 3. A complex schema usually has a top level table 302 containing key data for each data subject. Each record in this table 302 refers to a different data subject. The top level table 302 is a parent table, child tables can also be parents based on perspective. Child tables 306 and 310 link to parent tables 302 on one or multiple keys. For each record in a parent table 302 there may be zero or more records in the child table 306 and 310. Information from related records, or example within a child table 306 and 310 about the same parent record are aggregated into tables 308 and table 312. Information from child tables are aggregated into table 304. The aggregation process can be repeated for recursive data structures. Traversal method such as for example infix traversal may be utilized.

Aggregation of information within a record is often accomplished using aggregation of total knowledge or simple mutual information. Related record aggregation is applied to the information score from records within a single child table that are related to the same parent record (from the parent table). The following schemes may be used:

Total Information—The information in each record is summed to obtain the total information contained in all child records for the given parent. This is effectively aggregation of total information.

Maximum Adversary Power X—Select the X records with the most information in them related to the given parent as defined by the information score. Total (sum) the information in X records.

Average Adversary Power X—Calculate the arithmetic average information (u) in all elements related to the given parent. The information for the data element is=X*u Table Aggregation is applied to information scores from child tables (result of related records aggregation) relating to a single parent record. A parent record may have multiple child records in multiple child tables. The purpose of aggregation is to determine how much of this information from these child tables is aggregated up to the parent record. This resulting information is added to the information of the parent record.

Total Information—The information from each child table for this parent record is summed and added to the information of the parent record.

Maximum Table—Add the information from the child table, which has the high information contribution, to the parent record.

Figure 4:
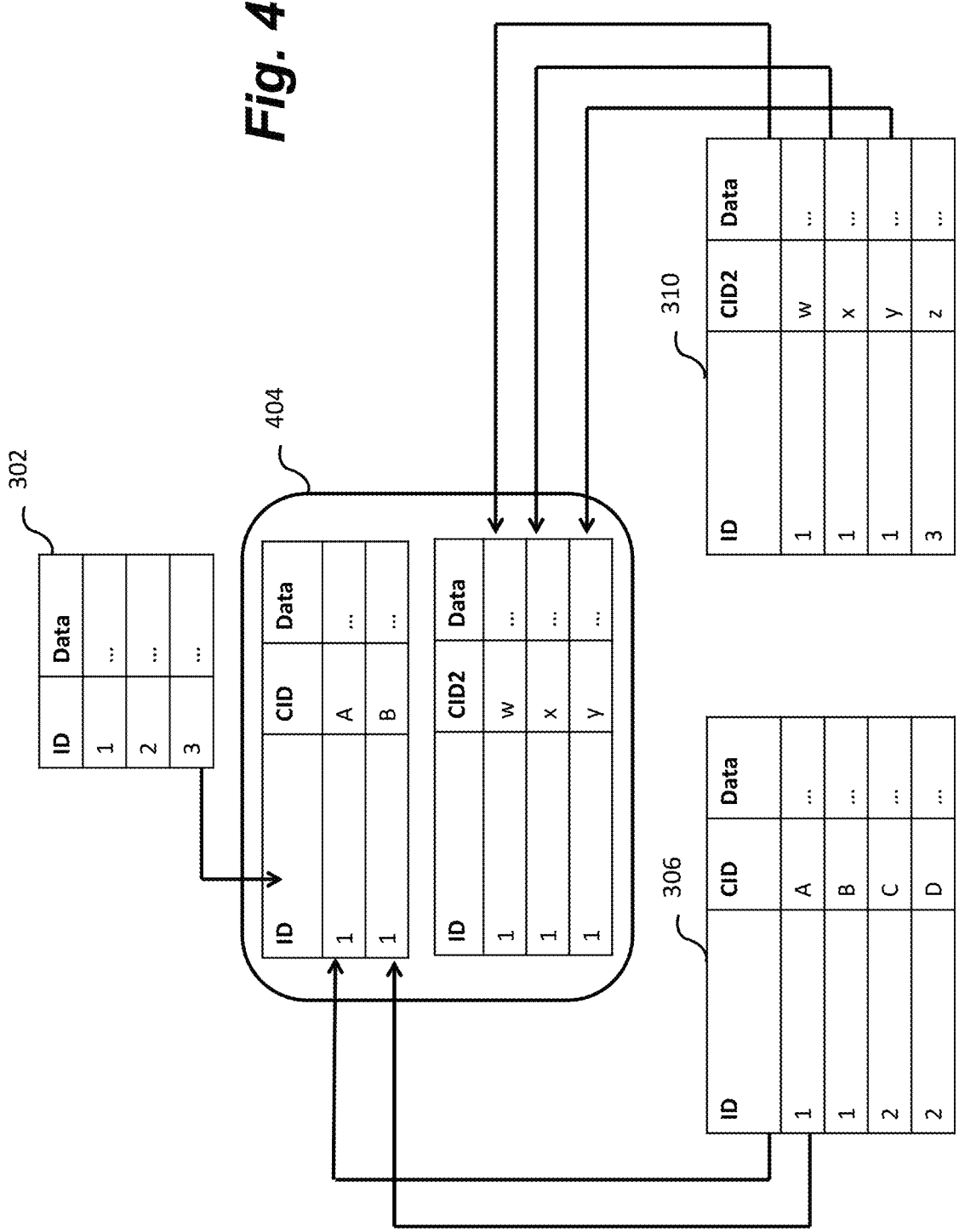
FIG. 4 shows another representation of a complex schema aggregation method.

FIG. 4 shows another representation of a complex schema aggregation method. The previous complex schema aggregation is particularly easy to implement and quite efficient on databases. A variation of the previous complex schema aggregation, allow better modelling of the risks associated with multiple tables. This is important when the event for adversary power may be spread across different tables, however this method is best implemented using subject profiles that are single data structure (not spread across different tables). In this method all related records from child tables 306 and 310 together are collected together into an aggregate table 404. The difference is related records are not combined from a single table into an information score, instead all records are pushed or included into a single collection of records (from child tables) and all child records identify what table they are from.

Aggregating all information from child records can be fulfilled by any methods described for related record aggregation, such as total power, average adversary power X, and maximum adversary power X. Note that now the adversary power aggregation would be over all child claims instead of limited to a single table.

The Back Fill Adversary Power is a variant of Average Adversary Power X; under many circumstances it behaves as average adversary power X and maximum Table would have behaved under the first aggregation scheme, however in case were the information is spread across different tables and adversary power X cannot be fulfilled by a single table, then it includes X events. For a given parent record (p) average adversary power X is calculated for each table. Recall that this method calculates a u, which is the average information in a QI. This algorithm will refer to $u_t$ as the information in an average data element for table t. The data element and information values are initially set to 0. While data element <X the highest contributing table (T) is selected that has not been processed yet and Y is the number of records in T that are about to be processed then information=min(X−data_elements, Y)*$u_t$ and data_elements=data elements+min (X−data_elements, Y) where the table T is marked as processed. Information about the amount of information aggregated from child tables is then processed.

Measuring mutual information requires joint distributions, which may not always be accessible to users of the method. A QI groups mechanism can be used to approximate known correlation by only including one of the correlated variables in the risk measurement. A group of QI is defined as a set of tuples table and column and effectively replaces these QIs (table and column) with a single pseudo QI. The pseudo QI must also have a place in the data structure (particular table that it will be placed into). The information score of the pseudo QI may be defined by many procedures. One procedure is that the information score of the pseudo QI is the maximum of information score of any QI contains within it (in the tuple of table and columns).

Figure 5:
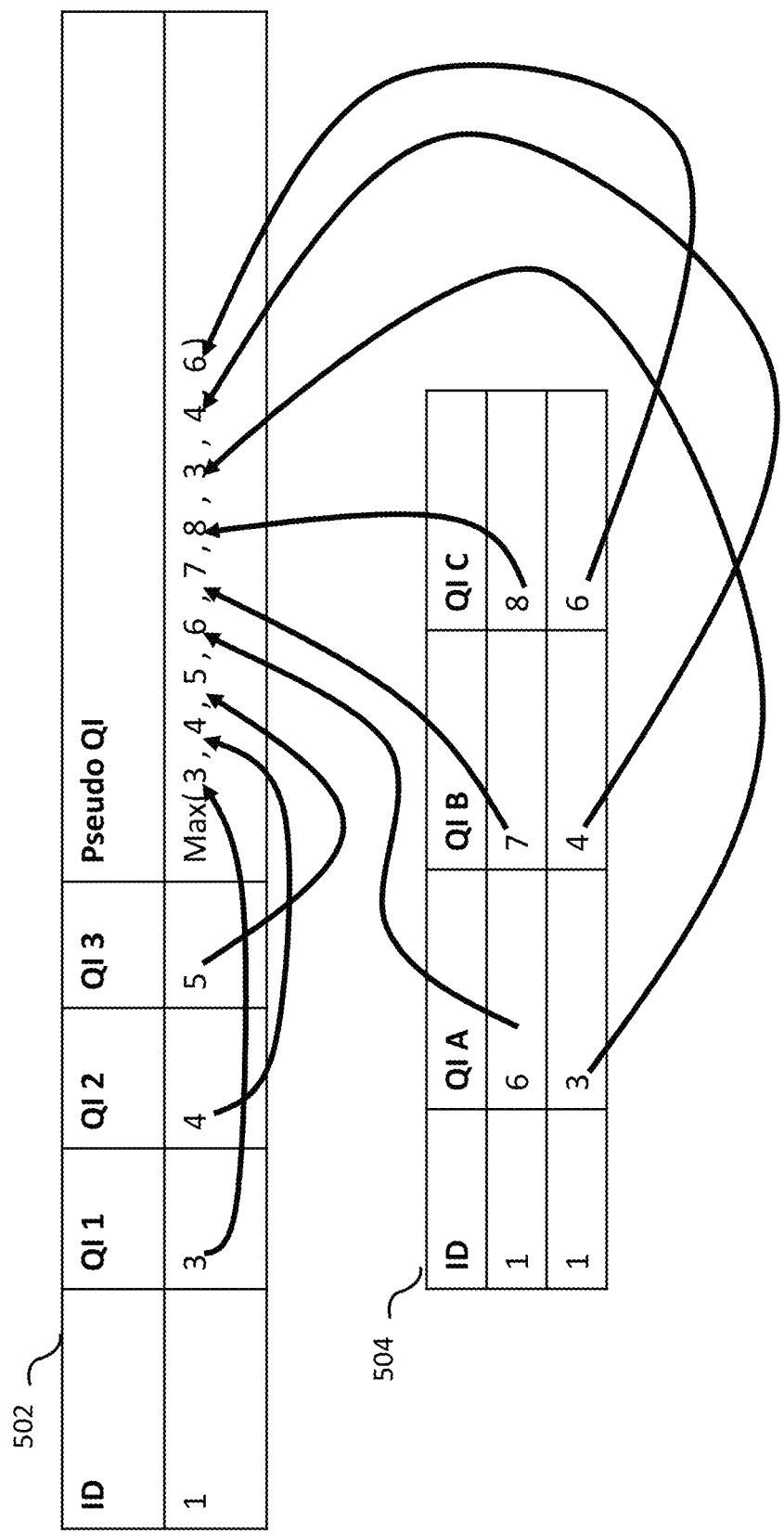
FIG. 5 illustrates quasi-identifier groups.

FIG. 5 illustrates QI groups. A single pseudo QI is created from Table 502 (QI 1, QI 2, and QI 3) and Table 504 (QI A, QI B and QI C). The resulting pseudo QI is the maximum of all of the information values. Creation of QI groups happens after assigning information scores to each value but before aggregating information scores. There are many uses of QI groups, one common structure in medical database will store the diagnosis encoding in multiple columns, depending on the encoding scheme (e.g. International Statistical Classification of Diseases (ICD)-9, ICD-10, multilingual European Registration Agency (MEDRA)). For any single record one or more of the columns may have values, however there is usually never a single completely populated column. Measuring the risk on a single sparse column would underestimate the risk. Measuring the risk on all columns would over-estimate the risk (including the same diagnosis multiple times if two encodings are present). Instead with a QI group the most information diagnosis will be used and the other encodes should be subsumed by this.

Alternatively probabilities may be utilized instead of information scores. First recall that information scores are $I(v)=-\log_2(pr(v))$, so an information score can be represented as a probability using $2^{-I(v)}=pr(v)$.

Figure 6:
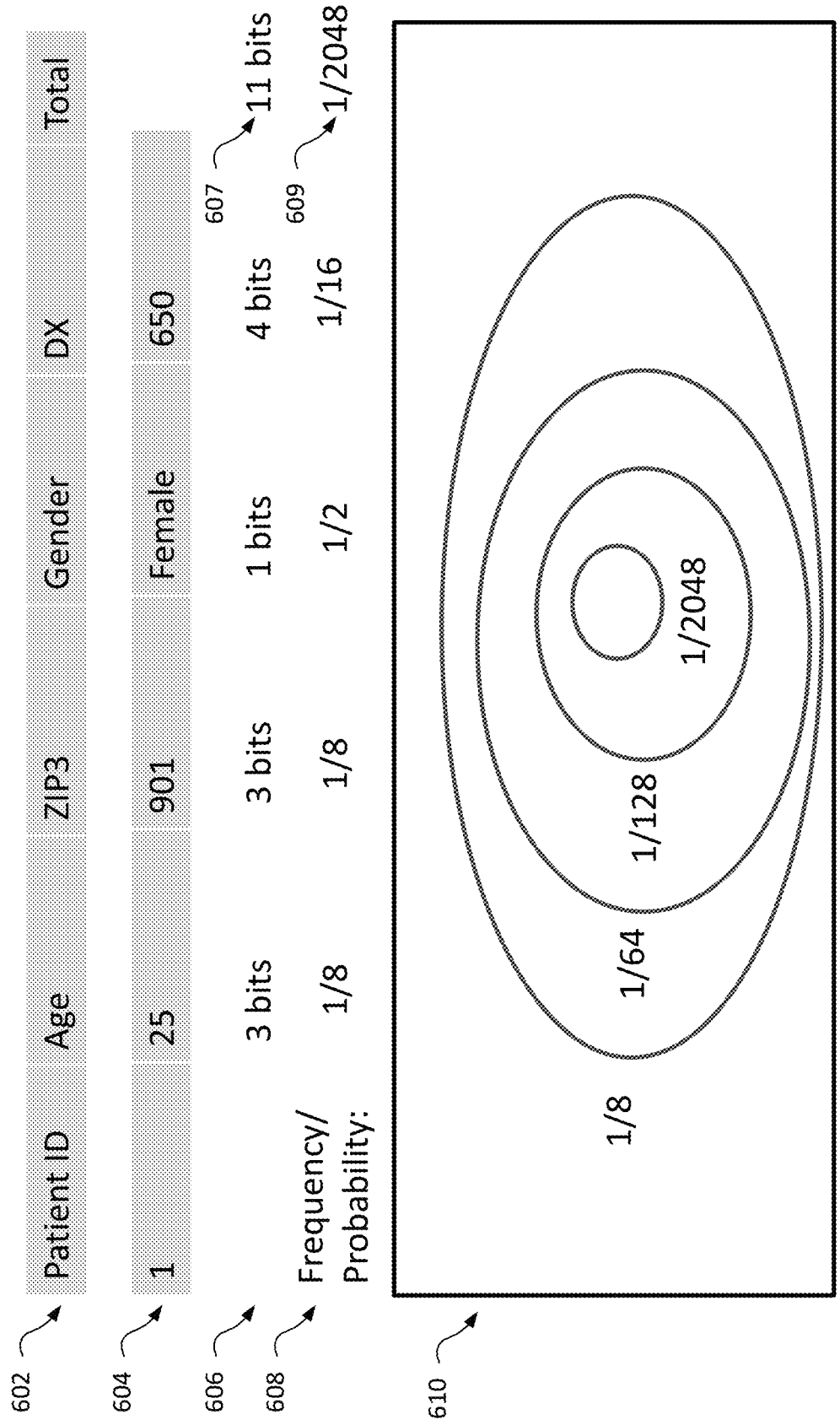
FIG. 6 illustrates measurement of information and probability on a simple subject profile.

FIG. 6 shows the parallel of using probability and information theory to estimate the risk of re-identification. The schema 602 identified the QIs that are present in a record. In this example patient ID, age, Zipcode, gender, and diagnosis. For the subject profile the data 604 provides the information associated with the subject record. Information scores 606 are assigned to each QI and then aggregate them into a total 607 which in this example is 11 bits. Probabilities 608 are assigned for each score and are aggregated into a product 609, which in this exampled is 1/2048. Graphic 610 illustrates how the inclusion of each QI narrows the possible number of population matches. When using probabilities a probability is assigned to each value, it is assumed that the distributions already return probabilities. The probabilities can then be aggregated where an addition on a logarithmic scale is the same as multiplication on a linear scale. It is a known mathematical identity $$I(a)+I(b)=-\log_2(pr(a)*pr(b))2^{-(I(a)+I(b))})=pr(a)*pr(b)$$

the result is $$\text{probability\_existance}=2^{-given\_bits}$$

An expected number of matching people in the population is calculated by:

$$\text{expected\_matches} = \frac{\text{population}}{\text{probability\_existance}}$$

The re-identification risk is then calculated by $$a = -\log_2(\text{expected\_matches})$$
$$k = \max(1, \text{expected\_matches})$$
$$\text{reid\_risk} = \min\left(1, \frac{1}{\text{expected\_matches}}\right)$$

Aggregation is then performed as previously described as the same re-identification metrics are provided.

Figure 7:
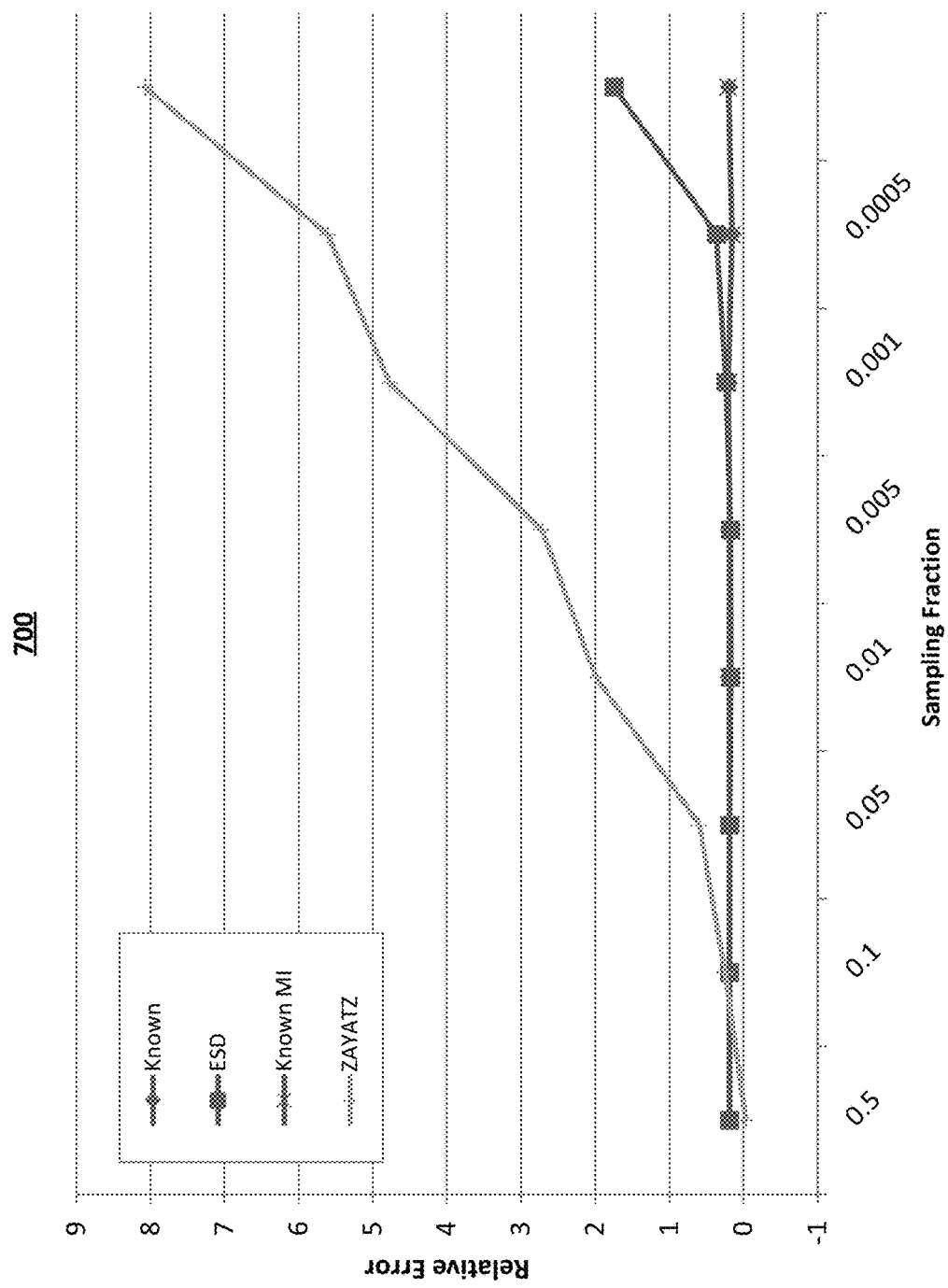
FIG. 7 shows a graph of the relative error of a low risk data set.
Figure 8:
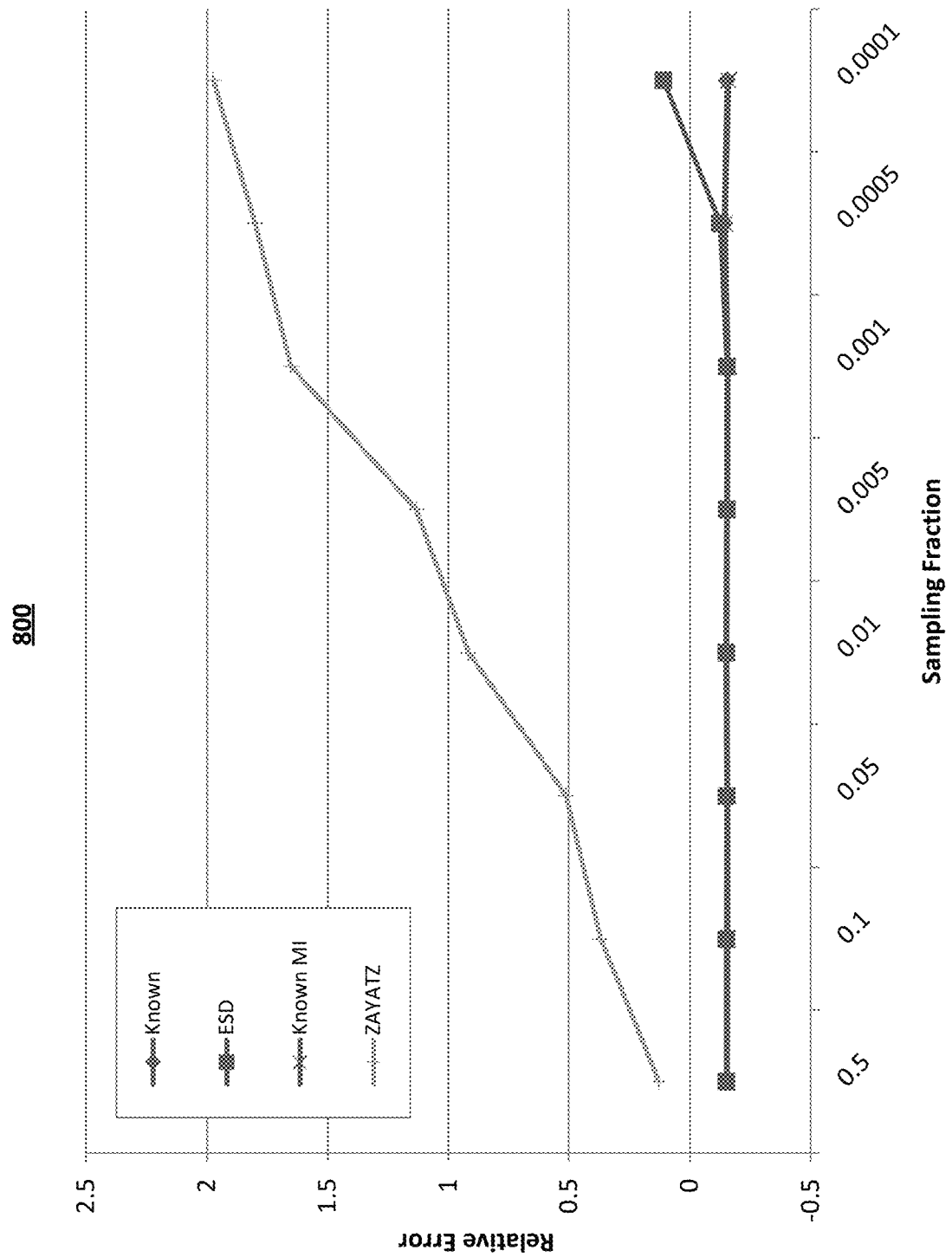
FIG. 8 shows a graph of the relative error of a medium risk data set.
Figure 9:
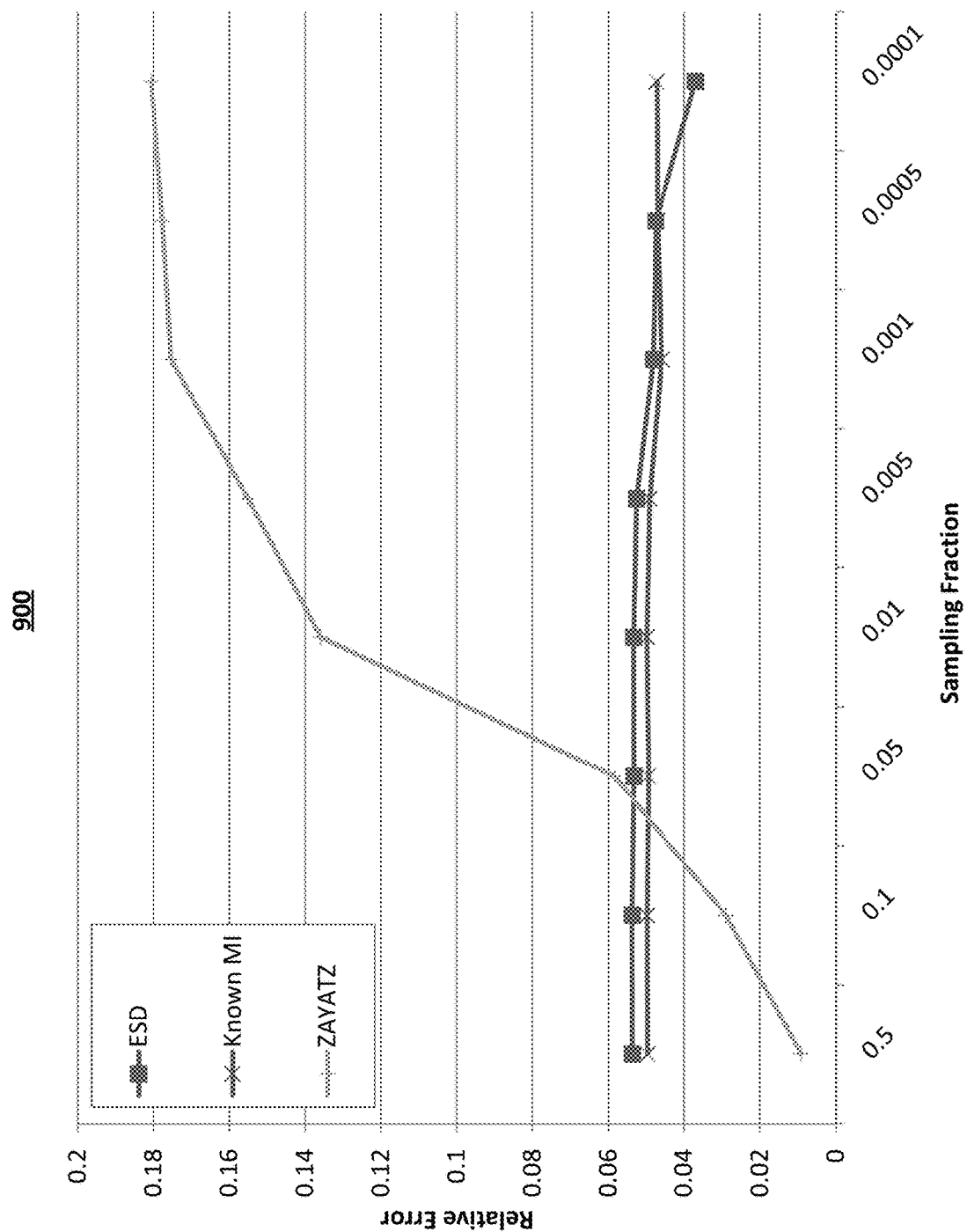
FIG. 9 shows a graph of the relative error of a high risk data set.

FIGS. 7 to 9 show the relative error of some methods when compared against the actual population risk and varying the sampling fraction. FIG. 7 shows a graph 700 of a low risk dataset plotted results are estimate sample distribution (ESD), simple mutual information (MI known), using known population distributions (known), and the Zayatz-Korte method (currently one of the most accurate estimation techniques). FIG. 8 show a graph 800 of a medium risk data and FIG. 9 show a graph 900 of a high risk data set. As shown the Zayatz-Korte method often has much higher relative error than the ESD. Further the Zayatz-Korte method shows an increase in risk as sampling fraction decreases. In contrast the ESD method provides consistent results almost without regard for sampling fraction. The ESD method provides conservative estimates on the high risk data shown in FIG. 9 when compared to the baseline.

Figure 10:
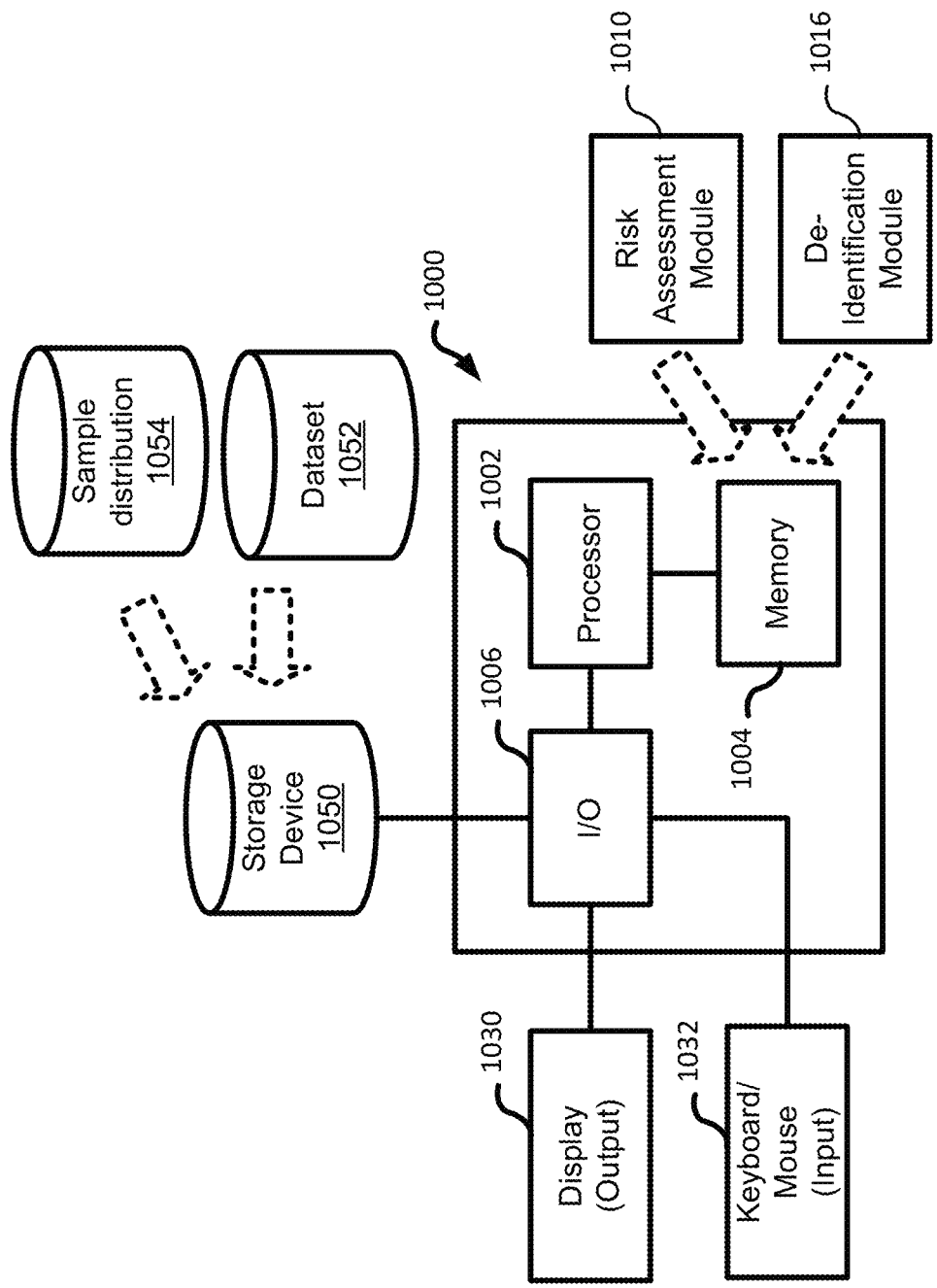
FIG. 10 shows a system for determining re-identification risk.

FIG. 10 shows a system for performing risk assessment of a dataset. The system 1000 is executed on a computer comprising a processor 1002, memory 1004, and input/output interface 1006. The memory 1004 executes instruction for providing a risk assessment module 1010 which performs an assessment of re-identification risk. The risk assessment may also include a de-identification module 1016 for performing further de-identification of the database or dataset based upon the assessed risk. A storage device 1050, either connected directly to the system 1000 or accessed through a network (not shown) which stores the dataset 1052 and possibly the sample population distribution 1054 (from which the dataset is derived). A display device 1030 allows the user to access data and execute the risk assessment process. Input devices such as keyboard and/or mouse provide user input to the I/O module 1006. The user input enables selection of desired parameters utilized in performing risk assessment, but may also be selected remotely through a web-based interface. The instructions for performing the risk assessment may be provided on a computer readable memory. The computer readable memory may be external or internal to the system 1000 and provided by any type of memory such as read-only memory (ROM) or random access memory (RAM). The databases may be provided by a storage device such compact disc (CD), digital versatile disc (DVD), non-volatile storage such as a hard-drive, USB flash memory or external networked storage. One or more components of the system or functions of the system may be performed, accessed, or retrieved remotely through a network.

Each element in the embodiments of the present disclosure may be implemented as hardware, software/program, or any combination thereof. Software codes, either in its entirety or a part thereof, may be stored in a computer readable medium or memory (e.g., as a ROM, for example a non-volatile memory such as flash memory, CD ROM, DVD ROM, Blu-ray™, a semiconductor ROM, USB, or a magnetic recording medium, for example a hard disk). The program may be in the form of source code, object code, a code intermediate source and object code such as partially compiled form, or in any other form.

It would be appreciated by one of ordinary skill in the art that the system and components shown in FIGS. 1-10 may include components not shown in the drawings. For simplicity and clarity of the illustration, elements in the figures are not necessarily to scale, are only schematic and are non-limiting of the elements structures. It will be apparent to persons skilled in the art that a number of variations and modifications can be made without departing from the scope of the invention as defined in the claims.

The present disclosure provided, for the purposes of explanation, numerous specific embodiments, implementations, examples and details in order to provide a thorough understanding of the invention. It is apparent, however, that the embodiments may be practiced without all of the specific details or with an equivalent arrangement. In other instances, some well-known structures and devices are shown in block diagram form, or omitted, in order to avoid unnecessarily obscuring the embodiments of the invention. The description should in no way be limited to the illustrative implementations, drawings, and techniques illustrated, including the exemplary designs and implementations illustrated and described herein, but may be modified within the scope of the appended claims along with their full scope of equivalents.

While several embodiments have been provided in the present disclosure, it should be understood that the disclosed systems and components might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

The invention claimed is:

1. A method for estimating a re-identification risk to one of a plurality of subjects, each separately described in a respective subject profile in a dataset, the method comprising:
   on a processor connected to a network and the dataset:
   retrieving a population distribution determined for each of the one or more quasi-identifying fields in the subject profile, wherein the population distribution aps a value in the each quasi-identifying field to a probability of at least one of the plurality of subjects having this value;
   assigning an information score to the each mapped value in the one or more quasi-identifying fields in the subject profile, wherein the information score is defined by a plurality of information bits in the mapped value;

aggregating the assigned information scores of all the mapped values in the one or more quasi-identifying fields in the subject profile;

estimating the re-identification risk to the one subject, based on
- a plurality of re-identification bits, wherein the plurality of re-identification bits is a function [$\log_2$] of a population,
- an anonymity value, wherein the anonymity value is based on the aggregated assigned information scores and the plurality of re-identification bits, and
- a re-identification metric for the subject based on the anonymity value; and lowering the re-identification risk to the one subject by performing further de-identification of the dataset based upon the estimated re-identification risk.

2. The method of claim 1, wherein the population distribution is a variable.

3. The method of claim 1, further comprising a step of creating an aggregate result of a plurality of re-identification metrics for a plurality of subject profiles in the dataset.

4. A system for estimating re-identification risk to one of a plurality of subjects, each separately described in a respective subject profile in the a dataset, the system comprising:
a hardware processor connected to a network and the dataset, the processor is configured to: retrieve a population distribution determined for each of the one or more quasi-identifying fields described in the subject profile, wherein the population distribution maps a value in the each quasi-identifying field to a probability of at least one of the plurality of subjects having this value;

assign an information score to the each mapped value in the one or more quasi-identifying fields in the subject profile, wherein the information score is defined by a plurality of information bits in the mapped value; aggregate the assigned information scores of all the mapped values of-in the one or more quasi-identifying fields in the subject profile; and calculate estimate the re-identification risk to the one subject based on a plurality of re-identification bits, wherein the plurality of re-identification bits is a function [$\log_2$] of a population, an anonymity value, wherein the anonymity value is based on the aggregated plurality of assigned information scores and the plurality of re-identification bits, and a re-identification metric for the subject based on the anonymity value; and lower the re-identification risk to the one subject by performing further de-identification of the dataset based upon the estimated re-identification risk.

5. The system of claim 4, wherein the processor is further configured to creating an aggregate result of a plurality of re-identification metrics for a plurality of subject profiles in the dataset.

6. The system of claim 5, wherein the aggregate result is a matrix.

7. The method of claim 3, wherein the aggregate result is a matrix.

8. The method of claim 1, wherein the aggregate of the assigned information scores is a summation of the plurality of assigned information bits of the information score of each value in the subject profile.

9. The method of claim 8, wherein the summation is a total information value of all child records for the subject profile.

10. The method of claim 1, wherein the subject profile comprises at least one record, and the method further comprising steps of:
aggregating the assigned information scores within each value in the at least one record;
aggregating the plurality of assigned information scores from values related to child tables associated with the record; and
aggregating the plurality of assigned information scores from values in the child tables.

11. The method of claim 1, further comprising a step of selecting predefined values of the one or more quasi-identifying fields with the most information related to a given parent as determined by the plurality of assigned information bits.

12. The method of claim 1, further comprising a step of calculating an arithmetic average information (u) of the plurality of assigned information bits in values of all elements related to the subject profile.

13. The method of claim 1, wherein the re-identification metric is further defined by any of a value associated with anonymity, equivalence class size, and re-identification risk.

14. The method of claim 1, further comprising steps of:
assigning a probability to each of the assigned information score defined by the plurality of information bits, aggregating the assigned probabilities; and
evaluating the ability to unambiguously link a record in one dataset to identify a matching subject in another dataset.

15. The method of claim 1, wherein the anonymity value is a metric measured in bits, where
if the anonymity value is greater than zero there are many subjects matching in the population,
if the anonymity is equal to zero the subjects is unique in the population, and
if the anonymity value is less than zero the subjects is unlikely to exist in the dataset or population.

16. The method of claim 15, further comprising a step of generating a histogram from a plurality of calculated anonymity values to estimate a number of unique subjects in the dataset.

17. The system of claim 4, wherein the population distribution is a variable.

* * * * *

UNITED STATES PATENT AND TRADEMARK OFFICE
CERTIFICATE OF CORRECTION

PATENT NO. : 10,685,138 B2
APPLICATION NO. : 15/320240
DATED : June 16, 2020
INVENTOR(S) : Scaiano et al.

It is certified that error appears in the above-identified patent and that said Letters Patent is hereby corrected as shown below:

On the Title Page

Page 2, item (56), Column 2, under "References Cited – OTHER PUBLICATIONS", Line 23, replace "pges" with "pages".

In the Specification

In Column 6, Line 1, replace "ask=$2^{max(a,0)}$" with "as k=$2^{max(a,0)}$".

In Column 7, Line 12, after "where" and before "is", replace "1" with "l".

In Column 8, Lines 3 and 4, after "by" and before "determining", add "collecting".

In Column 8, Line 12, after "CommonValues", add "--.--".

In Column 8, Line 13, after "values" and before "is", replace "(Estimated Values)" with "(EstimatedValues)".

In Column 9, Line 23, after "bits)" and before "can", add "that".

In Column 9, Line 32, after "bits)" and before "can", add "that".

In Column 9, Lines 59-62, add a line break in "average = $k(v1)k(v2)2^{I(v1)I(v2)\text{-reid\_bits}}+k(v1)(1-k(v2))2^{I(v1)\text{-reid\_bits}}+(1-k(v1))k(v2)2^{I(v2)\text{-reid\_bits}}+(1-k(v1))(1-k(v2))2^{\text{-reid\_bits}}$ average=$2^{\text{-reid\_bits}}(k(v1)2^{I(v1)}+1-k(v1))(k(v2)2^{I(v2)}+1-k(v2))$" as
"average = $k(v1)k(v2)2^{I(v1)I(v2)\text{-reid\_bits}}+k(v1)(1-k(v2))2^{I(v1)\text{-reid\_bits}}+(1-k(v1))k(v2)2^{I(v2)\text{-reid\_bits}}+(1-k(v1))(1-k(v2))2^{\text{-reid\_bits}}$
average=$2^{\text{-reid\_bits}}(k(v1)2^{I(v1)}+1-k(v1))(k(v2)2^{I(v2)}+1-k(v2))$".

Signed and Sealed this
Fifteenth Day of September, 2020

Andrei Iancu
*Director of the United States Patent and Trademark Office*

In Column 13, Line 4, add a line break in "I(a)+I(b)=-log$_2$(pr(a)*pr(b))2$^{-(I(a)+I(b))}$))=pr(a)*pr(b)" as
"I(a)+I(b)=-log$_2$(pr(a)*pr(b))
2$^{-(I(a)+I(b))}$))=pr(a)*pr(b)".

In the Claims

In Column 14, Line 61, In Claim 1, Line 8, after "distribution" and before "a value", replace "aps" with "maps".

In Column 15, Line 25, In Claim 4, Line 3, after "in" and before "a", delete "the".

In Column 15, Line 29, In Claim 4, Line 7, after "fields" and before "in", delete "described".

In Column 15, Line 39, In Claim 4, Line 17, after "values" and before "the", delete "of-".